United States Patent [19]

Fawzi et al.

[11] Patent Number: 5,068,110
[45] Date of Patent: Nov. 26, 1991

[54] STABILIZATION OF ENTERIC COATED DOSAGE FORM

[75] Inventors: Mahdi B. Fawzi, Flanders; Daniel A. Kubert, Lafayette; Kuchi S. Murthy, Morris Plains, all of N.J.

[73] Assignee: Warner-Lambert Co., Morris Plains, N.J.

[21] Appl. No.: 379,727

[22] Filed: Jul. 14, 1989

Related U.S. Application Data

[63] Continuation of Ser. No. 102,179, Sep. 29, 1987, abandoned.

[51] Int. Cl.$^5$ ................................................ A61K 9/62
[52] U.S. Cl. ..................................... 424/461; 424/462
[58] Field of Search ..................... 427/3; 424/463, 480, 424/482

[56] References Cited

U.S. PATENT DOCUMENTS

| | | | |
|---|---|---|---|
| 4,001,390 | 1/1977 | Ohno et al. | 424/480 |
| 4,176,175 | 11/1979 | Maekawa et al. | 427/3 |
| 4,287,221 | 9/1981 | Tonedachi et al. | 424/459 |
| 4,457,907 | 7/1984 | Porter | 424/497 |
| 4,600,645 | 7/1986 | Ghebre-Sellassie | 427/3 |
| 4,716,041 | 12/1987 | Kjornaes et al. | 427/3 |

FOREIGN PATENT DOCUMENTS

| | | |
|---|---|---|
| 881462 | 1/1980 | Belgium . |
| WO8300284 | 2/1983 | PCT Int'l Appl. . |
| 2043442 | 1/1980 | United Kingdom . |

OTHER PUBLICATIONS

J. Baum, "Enteric coated aspirin today", J. Rheumatology 12, 829 (1985).
S. Pollet et al., "Aspirin dosing using 15 grain enteric coated tablets", J. Rheumatology, 12, 337 (1985).
P. L. Madan, "Sustained release drug delivery systems, Part IV–Oral Products", Pharm. Mfg. 2, 41 (1985).
R. E. Pendell, "From solvents to aqueous coatings", Drug Develop. Ind. Pharm., 10, 191 (1984).
K. S. Murthy et al., "Comparative Evaluation of Aqueous Enteric Polymers in Capsule Coatings", Pharm. Tech. 10 36 (1986).
EPO Search Report with attachments.

*Primary Examiner*—Thurman K. Page
*Assistant Examiner*—Leon R. Horne
*Attorney, Agent, or Firm*—Joan Thierstein

[57] ABSTRACT

The present invention is a stabilized enteric-coated pharmaceutical dosage form and processes for the preparation thereof. Dissolution stability after storage of the dosage form under high stress conditions is improved by an enteric-coated dosage form having an enteric coating wherein the coating is of the acrylic resin kind of from 14 mg/cm$^2$ to 24 mg/cm$^2$ or an enteric coating wherein the coating is of the acetate kind of from 14 mg/cm$^2$ to 24 mg/cm$^2$ and having a second coating of hydrophilic coating for example, hydroxypropyl cellulose, hydroxymethyl cellulose or hydroxypropylmethyl cellulose.

8 Claims, 10 Drawing Sheets

STABILIZATION OF ENTERIC COATED DOSAGE FORM

This application is a continuation of Ser. No. 07/102,179, filed Sep. 29, 1987, now abandoned.

BACKGROUND OF THE INVENTION

Enteric coated dosage forms are well-known among products in the pharmaceutical industry.

In enteric coated products, the dosage form remains intact in the stomach, but dissolves and releases the active ingredient(s) in the upper intestine. The reasons for applying enteric coatings to oral solid formulations are (a) to protect the drug from the destructive action of the enzymes or low pH environment of the stomach e.g., erythromycin (b) to prevent nausea or bleeding associated with the irritation of the gastric mucosa as in the case of aspirin or potassium chloride and/or (c) to deliver the drug in an undiluted form in the intestine e.g., intestinal antibacterial agents or vermifuges. Based on these criteria, enteric coated products may be regarded as a type of delayed action dosage form. They differ from sustained release products in that with sustained release products, the drug release is extended over a period of time to maintain therapeutic blood levels and to decrease the incidence of side effects caused by a rapid release; whereas, with enteric coatings, the primary objective is to confine the release of the drug to a predetermined region of the gastrointestinal tract. Some of the enteric coated preparations currently sold in the United States are shown in the following Table 1.

TABLE I

| Product | Drug | Enteric Coating Dosage Form | Manufacturer |
|---|---|---|---|
| Cotazyme-S ™ | Pancrealipase | Pellets in a Capsule | Organon |
| Depakote ® | Divalproex Sodium | Tablet | Abbott Laboratories |
| Dulcolax ® | Bisacodyl | Tablet | Boehringer Ingelheim |
| Easprin ® | Aspirin | Tablet | Parke-Davis |
| Ecotrin ® | Aspirin | Tablet | Menley & James |
| Eryc ® | Erythromycin | Pellets in a Capsule | Parke-Davis |
| Ery-Tab ® | Erythromycin | Tablet | Abbott Laboratories |
| PCE ™ | Erythromycin | Polymer Coated Particles in a Tablet | Abbott Laboratories |

In addition to the advantages cited above, enteric coated dosage forms can fulfill a distinct need that arises frequently in drug discovery programs. During early stages of drug development i.e. in preclinical and early Phase I trials, some new chemical entities used in the health care industry present a challenge in testing for efficacy due to instability in gastric fluids or because of irritation in the gastrointestinal tract. In these situations, enteric coating of the encapsulated drug formulations would enable an investigator to determine the efficacy of the experimental drug free from the complications of gastric instability or irritation. The very limited amount of bulk material available during the early developmental stage and the fact that the chemical synthetic process has not been standardized preclude the manufacture of an optimized enteric coated pellet or tablet formulation for human or animal testing. Under these conditions, the benefits resulting from the availability of enteric coated capsule products are obvious, since the coating process will be independent of the capsule contents. Thus, the oral pharmacological and/or therapeutic efficacy of the new chemical entities can be ascertained without resorting to extensive formulation development studies which are costly, time-consuming, and, in many instances, infeasible at this point in the development of the new chemical entities.

While the currently marketed enteric coated dosage forms are either compressed tablets or pellets filled into capsules, a number of studies involving coated hard gelatin capsules have been reported in the literature. See Baum, J., "Enteric coated aspirin today", J. Rhumatology, 12, 829 (1985) and Pollet, S., White, R. H., Jang, H., Yim, C. W., and Feigal, D., "Aspirin dosing using 15 grain enteric coated tablets", J. Rhumatology, 12, 337 (1985). These involve the use of formalin-treated gelatin and shellac. Both of these natural materials suffer from the disadvantage of uncontrolled polymerization, during processing or storage, resulting in failure to release the drug in the small intestine.

An enteric product may fail to deliver the required performance due to either a lack of gastric resistance or through failure to release the active ingredient(s) in the intestine. In addition, erratic absorption was reported with some enteric coated products coated with shellac, although more recently marketed products were shown to provide reliable absorption. See Madan, P. L., "Sustained release drug delivery systems, Part IV—Oral products", Pharm. Mfg., 2, 41 (1985) and Pondell, R. E., "From solvents to aqueous coatings," Drug Develop. Ind. Pharm., 10, 191 (1984).

The chemical structure of the commonly used polymers for enteric coating purposes is shown as follows.

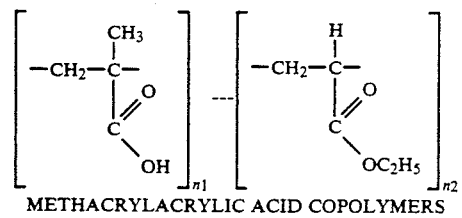
METHACRYLACRYLIC ACID COPOLYMERS

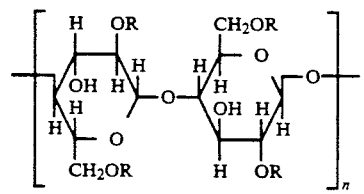

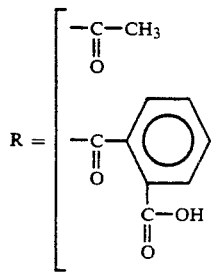
CELLULOSE ACETATE PHTHALATE

-continued

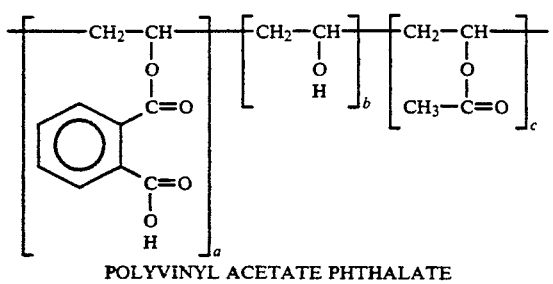

POLYVINYL ACETATE PHTHALATE

These contain ionizable carboxyl groups as an integral part of the molecule. The action of the enteric coating stems from a difference in the pH environments of the gastric and intestinal fluids. Within the low pH environment of gastric fluid, these polymers exist in their undissociated state and are insoluble. They ionize and become soluble as the pH rises to 5.0 and above in the intestinal fluids permitting dissolution and absorption of the active ingredient.

Traditionally, enteric polymers are applied onto substrates as solutions in organic solvents. The solvents commonly employed as vehicles are methylene chloride, ethanol, methanol, isopropyl alcohol, acetone, and combinations thereof. The choice of the solvent is based primarily on the solubility of the polymer, ease of evaporation, and viscosity of the solution. However, during the last decade, the use of organic solvents in pharmaceutical film-coating operations has come into disrepute because of high cost, flammability, toxicity of the residual solvent in the dosage form. These disadvantages spurred the exploration of suitable alternatives that ultimately lead to the commercial manufacture and availability of aqueous systems. Currently, three aqueous enteric polymer coatings are available for commercial use in the United States. These are Eudragit ® L30D (methacrylic acid-methacrylic acid ester copolymer marketed by Röhm-Haas GmBH, West Germany), Aquateric ® Cellulose Acetate Phthalate-containing product marketed by FMC Corporation, Philadelphia, Pa.) and Coateric TM (a polyvinyl acetate phthalate-based product marketed by Colorcon, Inc., West Point, Pa.). Unlike organic solutions, these aqueous-based systems can be prepared at high concentrations without encountering high viscosity.

It should be noted that the use of aqueous enteric coatings also involves certain liabilities. As a result of the low volatility of water, higher costs are associated with their use while drying the coats. Also, the presence of residual moisture may have a deleterious effect on the chemical and physical stability of the product as well as possibly providing a medium for microbial growth in some instances.

Previously the feasibility of preparing enteric coated capsules have been evaluated using the three commercially available aqueous latex polymeric dispersions (Eudragit ® L30D, Aquateric ®, and Coateric TM) and procainamide hydrochloride capsules as the model substrate. The effective range of coating levels was not established for the acrylic resins and their derivatives until the present inventor showed such levels. See Murthy, K. S., et al, "Comparative Evaluation of Aqueous Enteric Polymers in Capsule Coatings", Pharm. Tech., 10, 36 (1986). However, stability of the enteric coating comprising the acetates and their derivatives by high levels of coating proved to be less than desirable.

The present invention improves the stability of the capsules through the application of higher levels of coatings or by the application of higher levels of coatings in combination with the use of a protective coating. The stability characteristics of capsules coated with the aqueous dispersions according to the present invention are unexpectedly improved compared to similar coatings achieved through the use of organic solvents as well as known use of aqueous films for enteric coating. Coated capsules were stored under accelerated conditions, 37° C./80% RH and 45° C., for six to eight weeks. SEM examination and TMA analysis of coatings show the unexpectedly improved nature and characteristics of the films of the present invention.

Although a coating process which improves thermic and dimensional stability of capsules is taught in Belgian Patent 881,462 such a teaching does not make obvious the present invention use of a heavier enteric coating or a heavier enteric coating in combination with a further coating of an enteric dosage form. Also the present invention can be distinguished from the use of a water-soluble overcoat for alleviating tackiness and slow curing of sustained release dosage forms as found in the patents or applications in U.S. Pat. No. 4,600,645; WO83/00284; U.S. Pat. No. 4,176,175; and British 2043442. That is, the improvement of the overcoat and the sustained release formulation are different from the present inventions. Similarly, the present invention is readily distinguished from the treble layers required in U.S. Pat. No. 4,001,390 because in this disclosure the layers are not for an enteric dosage form as now set out in the present invention.

SUMMARY OF THE INVENTION

The present invention is a pharmaceutical dosage form having enteric coating comprising either an enteric coating having higher level of coatings or an enteric coating having higher levels of coatings in combination with an overcoat. The higher level of coating or higher level of coating with an overcoat provides improved dissolution stability at lower pH of the dosage form when stored under high stress conditions before use. The enteric coating of the present invention is from among those known in the art particularly having ionizable carboxyl groups as an integral part of the molecule. Enteric coatings of the present invention are those using aqueous systems in their use, i.e. manufacture. Such enteric coatings for which higher levels of coating are the invention may include acrylic resins and derivatives thereof such as the esters of polymethacrylic acids e.g. polymethylmethacrylate and such enteric coatings for which a higher level of coatings in combination with an overcoat is the present invention may include the acelates such as polyvinyl acetates or cellulose acetate phthalate, and polyvinyl acetate phthalate. Preferably the enteric polymers available as aqueous dispersions of acrylic resins are, for example, Eudragit ® L30D (containing polymethacryl methacrylate copolymer, and of the acetates are, for example, Aquateric ® containing cellulose acetate phthalate or Coateric TM polyvinyl acetate phthalate and the like.

A preferred embodiment of the present invention is an enteric-coated pharmaceutical dosage form having a high level of coating of Eudragit ® L30D or a high level of coating of either Aquateric ® or Coateric TM having an overcoat.

This invention also deals with a process that substantially eliminates the poor dissolution stability of enteric-coated pharmaceutical dosage forms when stored under high stress conditions.

In accordance with the invention, the product is first coated with a suitable polymer to condition the capsule surface in order to improve the adhesion of the enteric coat to the capsule. Then the capsules are coated, using the appropriate formulation to higher levels of enteric coating or using the appropriate formulation, i.e. having a higher level of enteric coating followed immediately by a water-soluble overcoat. Spraying is then terminated and the product temperature is elevated to the desired level. The process is continued until complete coalescence of the film is attained.

The optimum temperature and time to be used will depend upon the type of formulation, coating level and the type of polymeric dispersion. The overcoat is composed of a single agent or a combination containing one or more water-soluble, natural or synthetic polymers such as cellulosic derivatives, and polyethylene glycols.

The process of treating the dosage forms in accordance with the invention involves:

(1) coating a drug containing substrate with a precoat from among those known in the art to cause the enteric coating to adhere to the dosage form, such as hydroxypropyl cellulose or hydroxypropylmethyl cellulose;

(2) coating a drug-containing substrate with a high level of enteric coating formulation for polymethacrylates and their derivatives.

The process also involves steps (1) and (2) for the acetate enteric coatings and then (3) coating the product of step (2) with a water-soluble overcoat; and (4) recovering the treated dosage form.

The process of the invention includes a preferred embodiment of treating the dosage forms in accordance with (1) coating a drug containing substrate with a precoat (2 to 6 mg/cm$^2$) of an enteric coating formulation of from 14 mg/cm$^2$ to 24 mg/cm$^2$, preferably 14 mg/cm$^2$ to 16 mg/cm$^2$, when the enteric coating is polymethacrylates and their derivatives, and (2) recovering the treated dosage form.

In a more preferred embodiment, capsules are an enteric composition which contains methacrylacrylic acid copolymer, triethyl citrate, and water where the copolymer is a high level of coating, i.e. 14 mg/cm$^2$ to 24 mg/cm$^2$.

An overcoat formulation containing hydroxypropylmethyl cellulose, hydroxypropyl cellulose, and water is then applied to the capsules of acetate enteric coatings in another preferred embodiment. The over-coated capsules exhibit dissolution stability.

THE SUBSTRATE

Substrates which are enteric coated in accordance with the invention encompass a wide variety of materials. While it is preferred that they contained one or more drugs as the principle active ingredients, other ingestible substances, e.g. vitamins, minerals, nutrients and the like, all having better utility as an enterically coated substrate.

Pharmaceutical dosage forms are enteric coated to achieve one or more of the following objectives.

(a) To protect a drug from the destructive action of the enzymes or the low pH environment of the stomach (b) To prevent nausea or bleeding associated with the irritation by the drug of the gastric mucosa (c) To deliver a drug in an undiluted form to its absorption site in the intestine.

Useful drugs include certain analgesics, acid sensitive antibiotics, steroids, etc.

Preferred groups of drugs include aspirin, erythromycin, bisacodyl, and the like.

The drug-containing substrate can also include one or more of a wide variety of additives conventionally employed in solid dosage forms, e.g. carriers, flavor enhancers, colorants, and the like. When such additives are employed, they are present in such quantities that the quantity of active ingredient—e.g. drugs—which is present in the substrate is from about 5.0 to about 95.0 wt %, based on the total weight of the drug-containing substrate.

While the use of solid materials in the drug-containing substrate is preferred, the use of liquid ingredients, with or without suitable solid absorbents therefor, is also contemplated. The process of the invention is, with minor adjustment, suitable for treating liquid substrates.

THE ENTERIC COATING

By definition, enteric coatings are those which remain intact in the stomach, but will dissolve and release the contents of the dosage form once they arrive at the small intestine. Their purpose is to delay the release of drugs which are inactivated by the stomach contents, (e.g., pancreatin, erythromycin) or may cause nausea or bleeding by irritating the gastric mucosa (e.g., aspirin, steroids). In addition, they can be used to give a simple repeat-action effect where unprotected drug coated over the enteric coat is released in the stomach, while the remainder, being protected by the coating, is released further down the gastrointestinal tract.

The action of enteric coatings results from a difference in composition of the respective gastric and intestinal environments in regard to pH and enzymatic properties. Although there have been repeated attempts to produce coatings which are subject to intestinal enzyme breakdown, this approach is not popular since enzymatic decomposition of the film is rather slow. Thus, many modern enteric coatings are those which remain undissociated in the low pH environment of the stomach, but readily ionize when the pH rises to about 5 or above. The most effective enteric polymers are polyacids having a pK$_a$ of 3 to 5.

Historically, the earliest enteric coatings utilized formalin-treated gelatin, but this was unreliable since the polymerization of gelatin could not be accurately controlled, and often resulted in failure to release the drug even in the lower intestinal tract. Another early candidate was shellac, but again the main disadvantage was a potential to increase the degree of polymerization on storage, often resulting in failure to release the active contents. Although the pharmaceutical literature has contained references to many potentially suitable polymers, only three or four remain in use.

The most extensively used polymer is cellulose acetate phthalate (CAP) which is capable of functioning effectively as an enteric coating. However, a pH greater than 6 is required for solubility and thus a delay in drug release may ensue. It is also relatively permeable to moisture and gastric juice compared to most enteric polymers, thus susceptible to hydrolytic decomposition. Phthalic and acetic acids can be split off, resulting in a change in polymeric, and therefore enteric, properties. Another useful polymer is polyvinyl acetate phthalate (PVAP) which is less permeable to moisture and gastric juice, more stable to hydrolysis, and able to ionize at a lower pH, resulting in earlier release of actives in the duodenum.

A more recently available polymer is hydroxypropylmethyl cellulose phthalate. This has similar stability to PVAP and dissociates in the same pH range.

THE HYDROPHILIC OVERCOAT

The second coating composition, or overcoat, is designed to enhance the processability of the final product. It is the overcoat which significantly reduces the outlay in time and energy generally associated with treating the coated dosage forms.

The overcoat or second coating of the invention, like the first or base coat, is applied from an aqueous vehicle. The matrix of this second coating contains one or more hydrophilic, preferably highly water-soluble materials of monomeric or polymeric nature. One preferred matrix is hydroxypropyl cellulose. Other suitable matrices include hydroxypropylmethyl cellulose or methoxypropyl cellulose, and the like. Mixtures are operable.

The use of hydrophilic matrices is necessary when an overcoat is required.

To assist in the flow properties of this coating when applied and in the subsequent handling of the overcoated dosage form, conventional processing aids, e.g., surfactants, fillers, etc. can be employed. One preferred group of surfactants are silicon polymers.

Polyethylene glycols and other well-known hydrophobic polymers are highly preferred as additives. Polyethylene glycol 3350 is particularly preferred when aqueous hydroxypropylmethyl cellulose is the matrix.

Any of the optional ingredients employable in the base coating, described above, can be employed in the overcoat formulation. The amount of matrix material in the overcoat composition will range from about 0.01 to about 100% wt % based on total solids weight.

COATING PROCEDURES

The higher level or two steps coating process carried out in accordance herewith can be effected using conventional coating equipment. Suitable devices for applying the initial, or base, coating include fluidized bed and drying devices and the like. The one preferred device is the Aeromatic STREA Model 1, made by Aeromatic Inc., Towaco, N.J.

In order to save time in the overall process, it is preferred that, following the initial coating step, the base-coated substrate be allowed to sit, with optional heat treatment to temperatures of about 30° C. to about 45° C., and preferably about 35° C. to about 40° C., to coalesce the matrix particles, so that a useful film results. When heat is employed it is generally used for about fifteen to about sixty minutes, preferably about twenty to about forty minutes.

The application of the initial coat can be continued until the higher level of enteric coating, preferably about from 14 mg/cm$^2$ to 24 mg/cm$^2$ and most preferably about 15 mg/cm$^2$ is obtained. In any case the higher effective level may be determinedly the effect on the in vitro drug release in dissolution studies as described hereafter.

The application of the second, or overcoat, formulation can be carried out using the same equipment as was used for the base coat. One preferred embodiment requires the use of only one type of device with continuous coating steps.

The drying temperatures and times to be used on the overcoat will be about 30° to about 45° C., for about two to about fifteen minutes. Generally, preferred temperatures and times are about 30° to about 40° C., and about five to about ten minutes, respectively. The drying parameters used in treating the based coated intermediate—i.e., the product of step (1)—will be operable in this step as well.

Recovery of the final dosage form is carried out using conventional techniques. Once the overcoat has dried, the treated dosage forms are processed via well-known operations, such as are generally employed to accommodate packaging and/or storage requirements.

Other conventional techniques for handling oral dosage forms can be employed before, during and/or after the two-step process outlined above.

The chemical and physical nature of the substrate will dictate the final form which the preparations of this invention will take. For example, it is an excellent candidate for applicants' process.

While capsules are a preferred final product, other coated dosage forms, e.g. powders, ingestible pellets, tablets and the like, are also contemplated.

BRIEF DESCRIPTION OF THE DRAWINGS (RH is Relative Humidity)

FIG. 1: Effect of storage on the dissolution in 0.1N HCl of procainamide hydrochloride capsules coated with Eudragit ® L30D. Storage conditions: A Initial; B 25° C./80% RH/24 hours/open container; C 37° C./80% RH/8 weeks; D 45° C./8 weeks at 14.0 to 16 mg/cm$^2$ coating levels.

FIG. 2: Effect of storage on the dissolution in 0.05M phosphate buffer pH 6.8 of procainamide HCl capsules coated with Eudragit ® L30D. Storage conditions: A Initial; B 25° C./80% RH/24 hours/open container; C 37° C./80% RH/8 weeks; D 45° C./8 weeks at 14.0 to 16 mg/cm$^2$ coating levels.

FIG. 3: Effect of storage on the drug dissolution in 0.1N HCl of procainamide hydrochloride capsules coated with acrylic resin through organic solvent. Storage conditions: A Initial; B 25° C./80% RH/24 hours/open container; C 37° C./80% RH/6 weeks; D 45° C./6 weeks at 14.0 to 16 mg/cm$^2$ coating levels.

FIG. 4: Effect of storage on the drug dissolution in 0.05M phosphate buffer pH 6.8 of procainamide hydrochloride capsules coated with acrylic resin through a solution in organic solvent. Storage conditions: A Initial; B 25° C./80% RH/24 hours/open container; C 37° C./80% RH/6 weeks; D 45° C./6 weeks at 14 mg to 16 mg/cm$^2$ enteric coating level.

FIG. 5: Effect of storage on the drug dissolution in 0.1N HCl of procainamide hydrochloride capsules enteric coated with Aquateric Storage conditions: A Initial; B 25° C./80% hours/open container; C 37° C./80% RH/6 weeks; D 45° C./6 at 18 to 20 mg/cm$^2$ enteric coating level.

FIG. 6: Effect of storage on the drug dissolution in 0.05M phosphate buffer pH 6.8 of procainamide hydrochloride capsules enteric coated with Aquateric®. Storage conditions: A Initial; B 25° C./80% RH/24 hours/open container; C 37° C./80% RH/6 weeks; D 45° C./6 weeks at 18 to 20 mg/cm$^2$ enteric coating level.

FIG. 7: Effect of storage on the drug dissolution in 0.1N HCl of procainamide hydrochloride capsules coated with CAP through organic solution. Storage conditions: A Initial; B 25° C./80% RH/24 hours/open container; C 37° C./80% RH/6 weeks; D 45° C./6 weeks as previously known at normal coating levels.

FIG. 8: Effect of storage on the drug dissolution in 0.05M phosphate buffer pH 6.8 of procainamide HCl capsules coated with CAP through organic solution. Storage conditions: A Initial; B 25° C./80% RH/24 hours/open container; C 37° C./80% RH/8 weeks; D 45° C./8 weeks as previously known at normal coating levels.

FIG. 9: Effect of storage on the drug dissolution in 0.1N HCl of procainamide HCl capsules coated with Coateric TM Storage conditions: A Initial; B 25° C./80% RH/24 hours/open container; C 37° C./80% RH/6 weeks; D 45° C./6 weeks at 18 to 20 mg/cm² enteric coating level.

FIG. 10: Effect of storage on the drug dissolution in 0.05 M phosphate buffer pH 6.8 of procainamide HCl capsules coated with Coateric TM Storage conditions: A Initial; B 25° C./80% RH/24 hours/open container; C 37° C./80% RH/16 weeks; D 45° C./6 weeks at 18 to 20 mg/cm² enteric coating level.

The following examples demonstrate the effectiveness of the invention but are not meant to be limiting thereto.

DETAILED DESCRIPTION OF THE INVENTION

Materials and Methods

Figure 1:
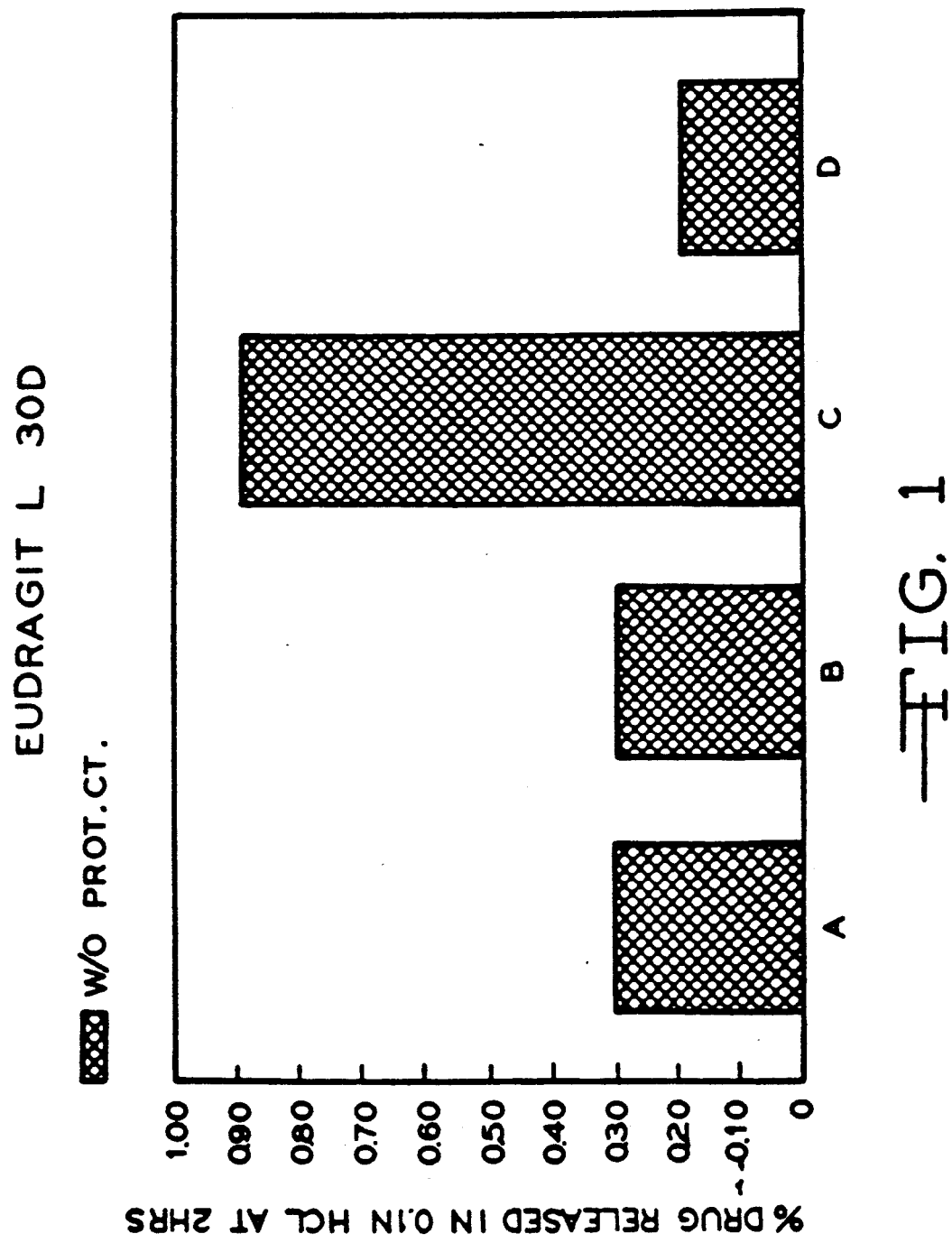

The following are used: Eudragit ® L30D, Aquateric ®, and Coateric TM (see the above definitions of each of these products). Cellulose acetate phthalate from Eastman Kodak, Rochester, N.Y. and used as received. Eudragit ® L30D is supplied as an aqueous dispersion containing 30% solids, while Aquateric ® and Coateric TM powders are reconstituted two hours prior to spraying. To all the dispersions, diethyl phthalate is added to yield a final concentration of 20% in the system. The role of diethyl phthalate is to plasticize the films. The organic solutions of polymers are prepared as follows:

Acrylic Resin: Twenty-four grams of Eudragit L 100 is dissolved through slow addition and continuous stirring into 240 ml of absolute ethanol. Six grams of diethyl phthalate is then added with continuous stirring.

Cellulose Acetate Phthalate: To 20 ml of acetone contained in a beaker, 24 g of cellulose acetate phthalate is added with constant stirring, followed by addition of 40 ml of absolute ethanol and 6 g of diethyl phthalate. The solution is stirred until a clear homogenous liquid is obtained.

Polyvinyl Acetate Phthalate: To 24 g of polyvinyl acetate phthalate, 210 ml of absolute ethanol is added with continuous stirring, followed by 10 ml of acetone and 20 ml of distilled water. After a clear solution is obtained, 6 g of diethyl phthalate was added and the solution is stirred until a clear liquid was present.

Hydroxypropyl Cellulose Solutions: These are prepared at 5% w/v concentration in distilled water. The weighed quantity of solid is added in small amounts, with vigorous and continuous agitation of the liquid until all the solid had dissolved.

Coating Procedure

Hydroxypropyl cellulose solutions are applied first on the capsules. The capsules are then dried for twenty-four hours at room temperature prior to the application of the enteric coat. In some experiments, a final protective coat of hydroxypropyl cellulose is applied to the capsules. Procainamide HCl 250 mg dose hard shell capsules serves as the cores. The composition the capsule blend used in these studies is described as follows in Table 2:

TABLE 2

| Composition of the Procainamide HCl Core Capsules | |
|---|---|
| | mg/cap |
| Procainamide HCl | 250 |
| Lactose USP Hydrous | 147 |
| Hydrogenated Vegetable Oil | 3 |
| TOTAL | 400 |

The coating experiments are conducted using a laboratory scale fluid bed equipment (Aeromatic STREA Model 1, Aeromatic Inc., Towaco, NJ). The operating conditions prevalent during the coating run are listed as follows in Table 3:

TABLE 3

| Equipment and Operating Conditions Employed During Fluid Bed Coating of Procainamide Hydrochloride Capsule | |
|---|---|
| Equipment: | Aeromatic STREA Model 1 |
| Outlet Temperature: | 25°–30° |
| Drying Temperature: | 25°–30° |
| Air Pressure: | 0.6–0.8 bar |
| Suspension Delivery Rate: | 1.0–2.0 ml/min |

Also the following Tables 4 and 5 show the Enteric Polymers used in the invention examples and the Composition of Coating Levels used in enteric coated capsules of the examples.

TABLE 4

| Enteric Polymers Used in the Study | |
|---|---|
| Eudragit ® | L30D (methacryl acrylic acid methacrylate copolymers) |
| Aquateric ® | (cellulose acetate phthalate) |
| Coateric TM | (polyvinyl acetate phthalate) |

TABLE 5

| Composition of Coating Levels Used in Enteric Coated Capsules | |
|---|---|
| Precoat (hydroxypropyl cellulose): | 4–6 mg/cm² |
| Enteric Coat: | 15–20 mg/cm² |
| Protective Finish Coat (hydroxypropyl cellulose): | 4–6 mg/cm² |

In a typical experiment, 200 capsules of procainamide HCl are loaded into the fluid bed coater. Hydroxypropyl cellulose solution is applied to achieve a weight increase of 4.0 to 6.0 mg/cm² or 16 to 25 mg/capsule. After drying the capsules in the fluid bed coater for fifteen minutes, they are allowed to cure at room temperature for twenty-four hours before the application of enteric coat. Where a protective outer coat was indicated, that is on those capsules for which a lower than effective higher level enteric coating is present, the capsules are again coated with hydroxypropyl cellulose solution. The final capsules are air dried for twenty-four hours to forty-eight hours prior to dissolution testing.

In capsule coating studies, the amount of coat applied is usually expressed as mg/cm$^2$ of capsule surface. A surface area value of 4.1 cm$^2$ for No. "1" size capsules is used in the current studies. The capsule coating levels are indicated in terms. of mg of coat per square centimeter of capsule surface.

The amount of coat applied to these capsules is 4.0 to 6.0 mg/cm$^2$ of precoat and 18 to 20 mg/cm$^2$ of enteric coat. Where a final seal coat is applied, it is present at a concentration of 4.0 to 6.0 mg/cm$^2$.

Dissolution Studies

The in vitro drug release from coated capsules is determined using the dissolution method outlined in the USP XXI for enteric coated dosage forms (Method B). This procedure involves exposure of the dosage form to 900 ml of 0.1N hydrochloric acid followed by testing in 0.05M phosphate buffer pH 6.8. The amount of drug in solution is determined spectrophotometrically from an aliquot of a filtered sample after appropriate dilution with 0.1N sodium hydroxide solution. An absorbance maximum at 273 nm with an absorptivity value of 62.0 g/liters-cm is used to calculate the amount of drug in solution at various time periods. There is no interference from diethyl phthalate in the UV assay. The dissolution values reported in the current investigations are the average of three to six individual determinations.

Scanning Electron Microscopy (SEM)

(a) Surface Specimens

A small amount of graphite cement (BioRad Laboratories, #1216, Watford, England) is applied to the flat surface of a clean pin-type aluminum mount (Structure Probe #1509, West Chester, Pa.). An intact c.psule is seated into the cement and allowed to air dry. The specimens are then placed into the SEM autocoater vacuum chamber (Polaron, Model E5200, Cambridge, Mass.) and sputter coated with gold-paladium alloy for 100 seconds.

(b) Cross-Sectional Specimens

Using fine microforceps, an intact capsule is immersed in liquid nitrogen for fifteen seconds. The frozen capsule is removed, placed in a glass evaporating dish, and fractured with a #20 scalpel. A clean section containing the capsule shell and all of the coating layers, is seated into the graphite cement, such that the cross section interface is revealed. SEM autocoating procedures described earlier are used.

The prepared specimens are loaded into the SEM chamber (Amray, Model 1200B, Bedford, Mass.). Examination of the capsule surface is performed at 100× using the backscattered mode (tile angle=20°, beam spot size=2), while examination of cross sectional specimens is carried out using the secondary electron mode at 250× (tilt angle=45°, beam spot size=7). Several fields of view are observed to obtain a representative photomicrograph.

Thermomechanical Analysis (TMA)

Thermomechanical analysis of the enteric films is conducted in a Perkin-Elmer TMS-2 analyzer (Perkin-Elmer, Norwalk, CT). To minimize the effect of capsule curvature in affecting initial probe height, a section of the coating is removed from the capsule and transversely cut into a 2 mm square. The section is placed into the sample tube chamber of the instrument. To maximize heat conductivity between furnace and sample, a blanket of helium gas is diffused through the chamber. A penetration probe and force load of 3 g is used. Samples are scanned from 30° C. to 200° C. at a rate of 5° C./minute. Changes in length relative to the original length are computed.

Differential Scanning Calorimetric Analysis (DSC)

Analysis of peeled films is performed using a Perkin-Elmer Model DSC-2C calorimeter (Perkin-Elmer, Norwalk, Conn.) in an inert nitrogen atmosphere at a scan rate of 5° C./min.

The stability of the capsules coated with different polymers is followed after storage for six to eight weeks at 37° C./80% RH and 45° C. in screw-capped high density polyethylene bottles. Experience shows that if a product is stable under such storage conditions, it can be expected to be stable under ambient conditions of storage for at least six months. This time period is considered adequate for testing samples in the clinic. In addition, some capsules are exposed to 80% RH at room temperature for twenty-four hours in open containers and their stability assessed.

Since the criterion for stability of an enteric coated dosage form is that it should not release a significant amount of the active ingredient in the stomach, but should dissolve completely in the higher pH environment of the intestine, in vitro dissolution stability is monitored in both 0.1N hydrochloric acid and 0.05M phosphate buffer pH 6.8. Based on earlier experience which indicates that lower levels of enteric coat are not adequate to prevent permeation of moisture or to withstand 45° C. temperatures, the capsules are coated to relatively high levels (e.g. in the range of 14.0 to 16.0 mg of EC/cm$^2$ of capsule surface). This is felt to be necessary in spite of the fact that current studies show that minimal levels of enteric coat necessary to provide the required gastric resistance with the various polymers via organic solution are: 11.0 mg/cm$^2$ Eudragit ® L 100, 2.1 mg/cm$^2$ CAP and 4.9 mg/cm$^2$ polyvinyl acetate phthalate.

Figure 2:
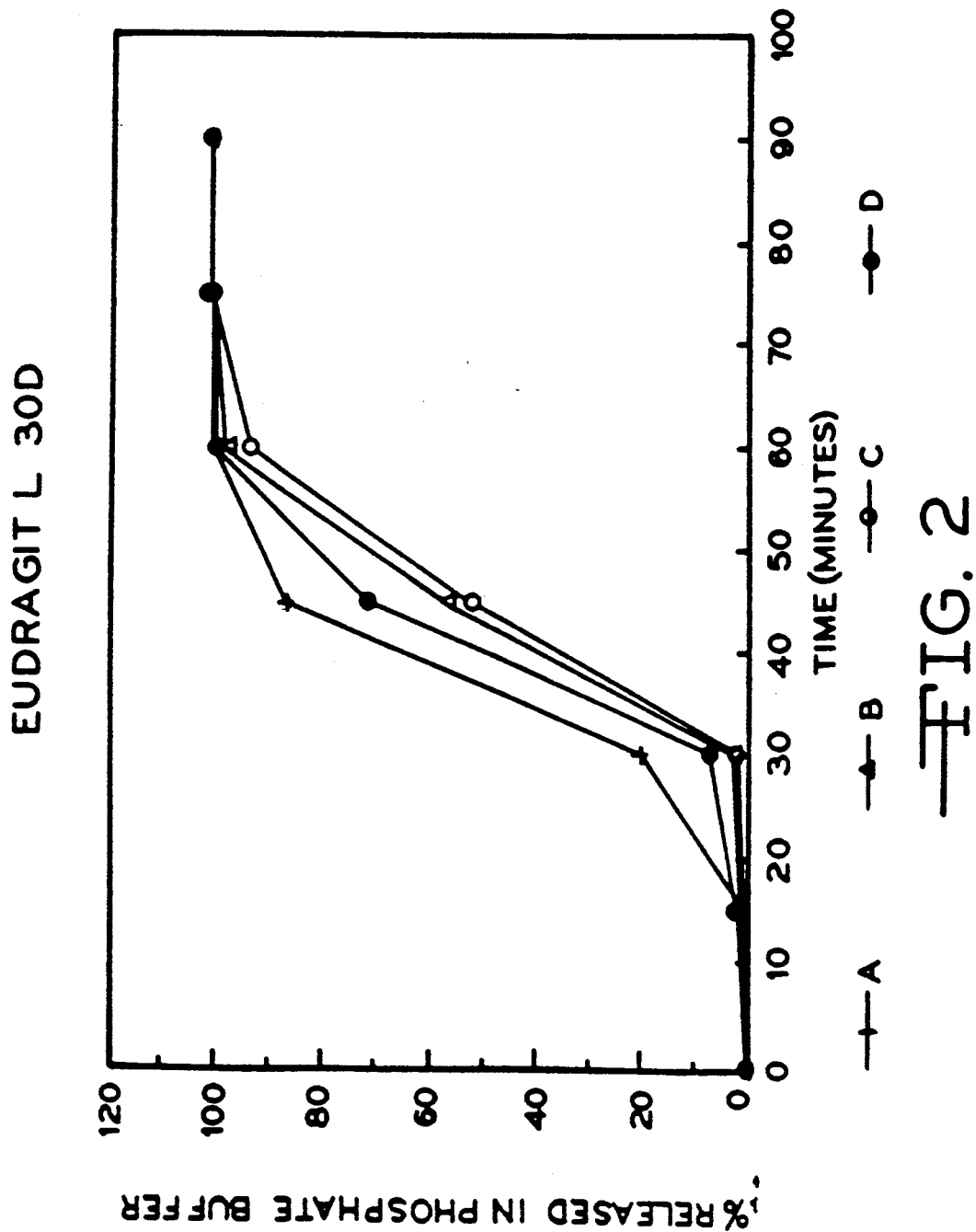

FIG. 1 illustrates the effect of storage on the in vitro drug release rates of procainamide HCl capsules coated with Eudragit ® L30D. Total absence of drug dissolution in 0.1N HCl after two hours is evident both at the time of preparation and after storage under the described conditions. There is a lag period of approximately thirty minutes before the dissolution of capsule shell occurred in phosphate buffer pH 6.8. Once the coating had dissolved, all the active content is in solution within thirty minutes (FIG. 2). The results of dissolution, both in 0.1N HCl and phosphate buffer pH 6.8, are about the same with or without the presence of protective outer coat, if higher levels of coating are present (D). Thus, a protective coat is not needed in the system having critical higher coat levels. Previous findings on Eudragit ® L30D coated capsules indicated that low levels of enteric coat are not sufficient to protect the product when stored at 45° C.. That is, surprisingly 14.0 to 16 mg/cm$^2$ are effective in maintaining the product stability at 45° C. for at least two months.

Figure 3:
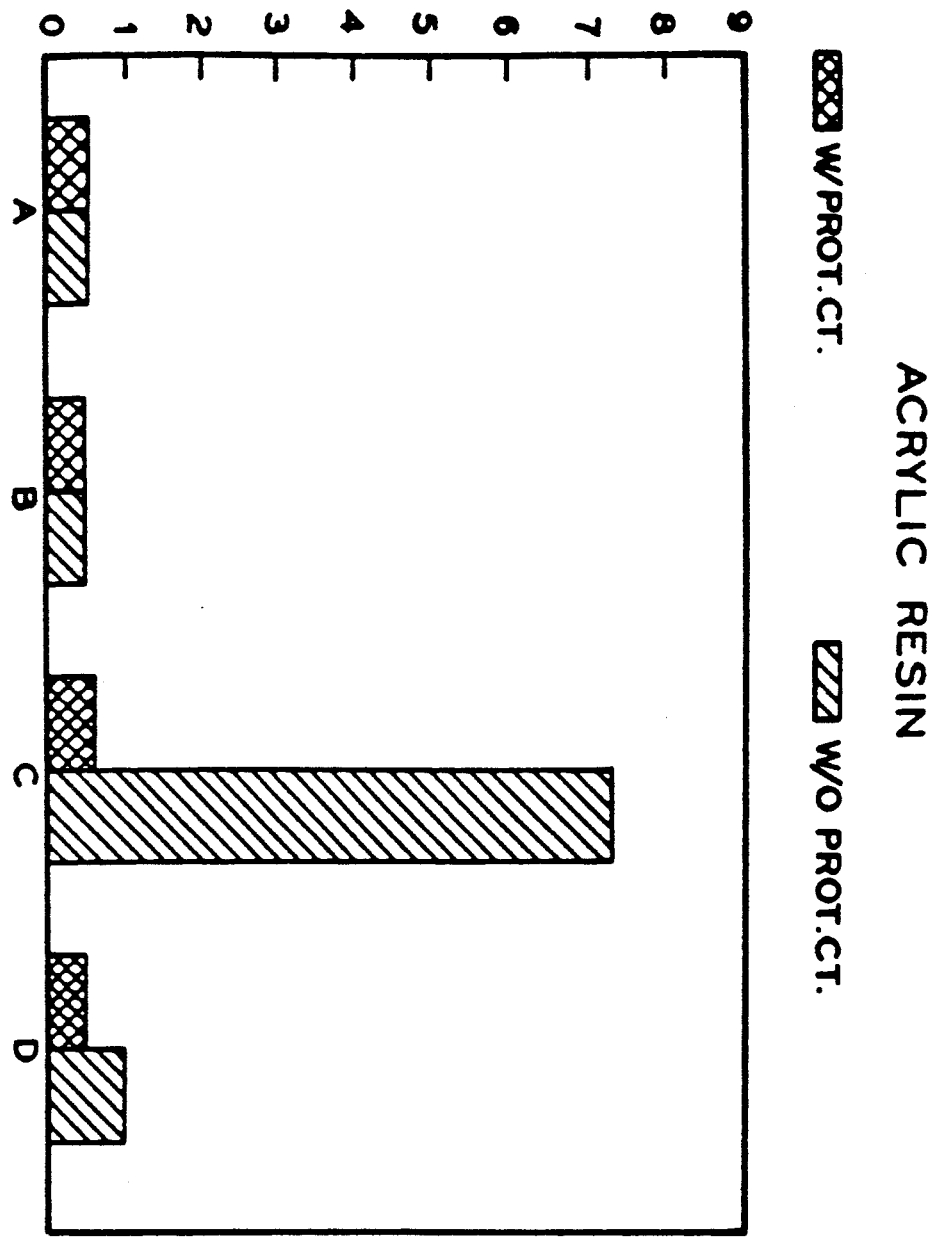
Figure 4:
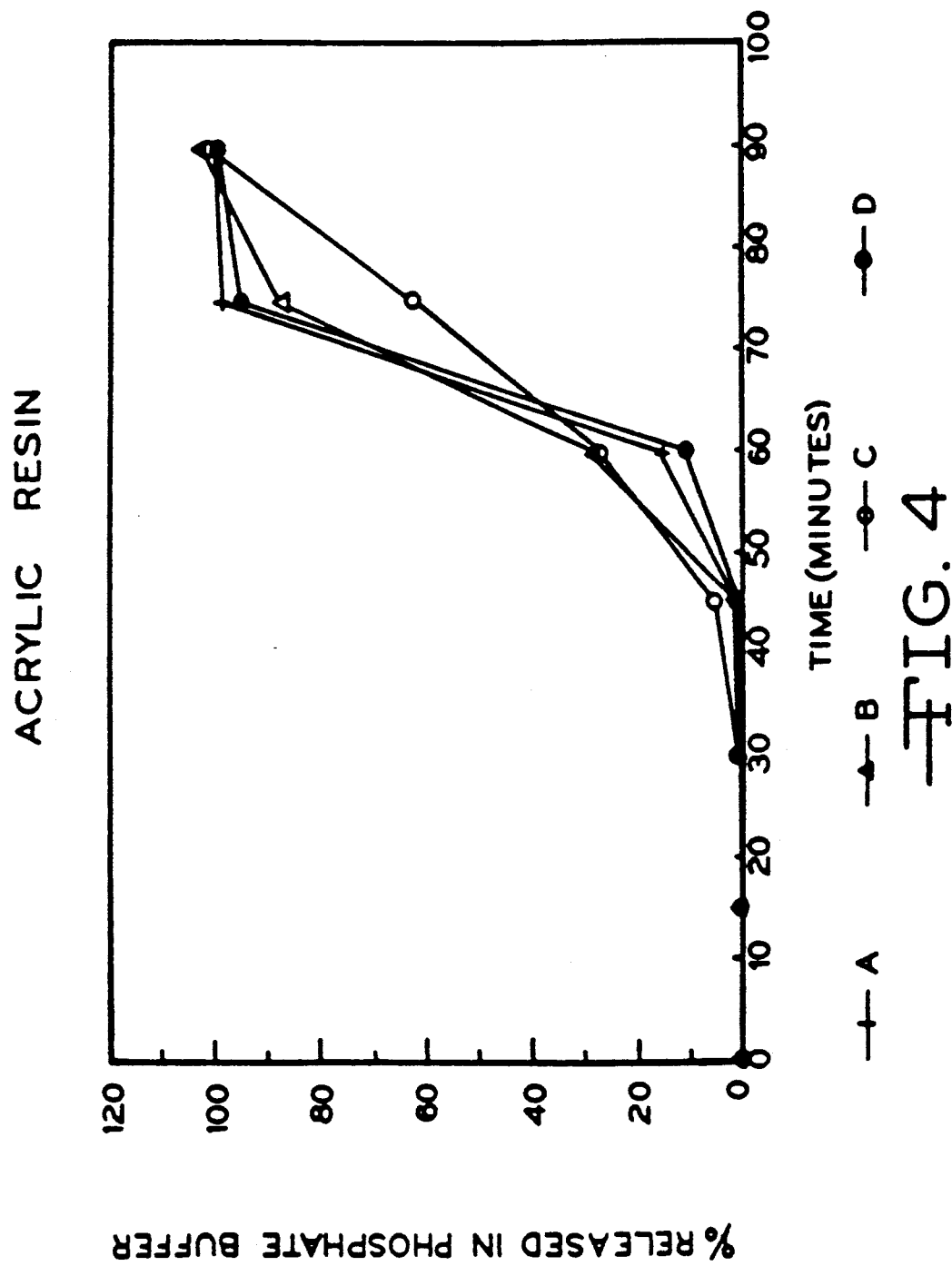

FIGS. 3 and 4 display data on the release and stability characteristics of capsules coated with the acrylic resin applied through an organic solution. In the absence of a final seal coat, the in vitro release of the coated capsules stored at 37° C./80% RH show low gastric resistance. Nearly 7.0% of the drug is in solution in 0.1N HCl at two hours. In addition, the dissolution of these capsules is initially slow in pH 6.8 buffer. It took nearly forty-five minutes of exposure in this medium before the coating dissolves. Use of protective seal coat of hydroxypropyl cellulose, however, yield coatings which are stable under accelerated storage conditions.

Figure 5:
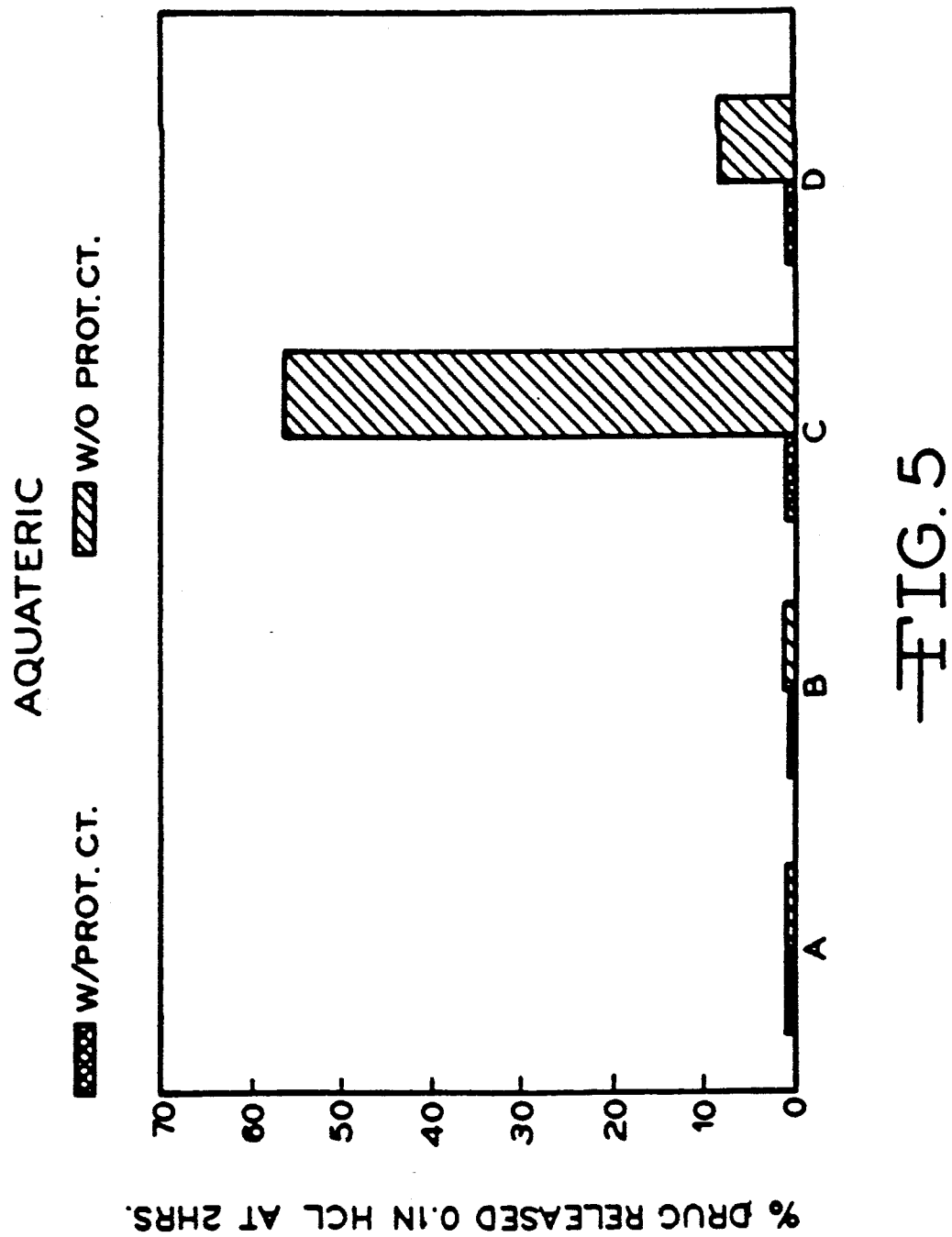
Figure 6:
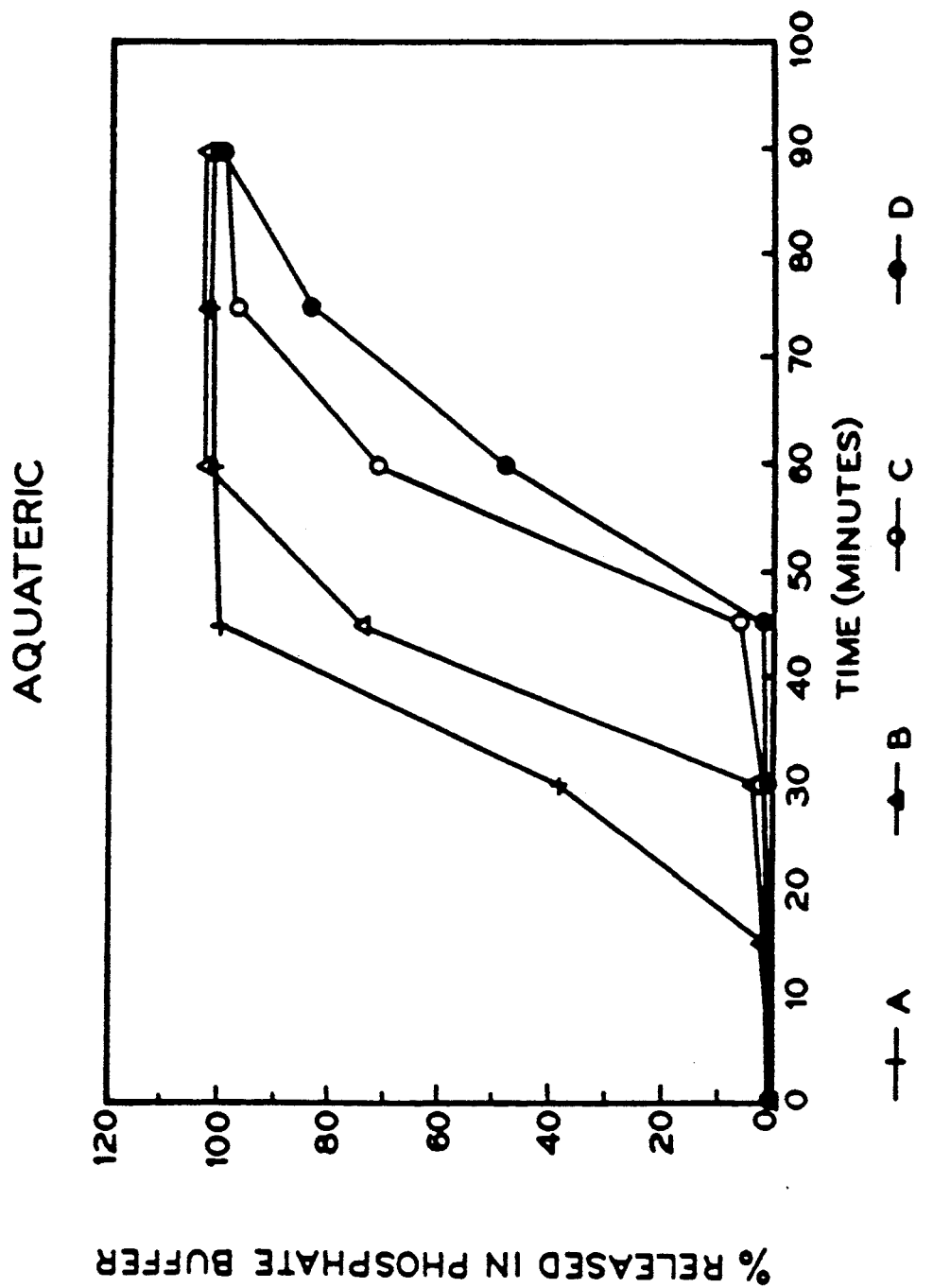

The results of storage stability studies performed on Aquateric ® coated capsules are shown in FIGS. 5 and 6. The influence of protective hydroxypropyl cellulose coating on the stability of the product is dramatically illustrated by the data presented in FIGS. 6 and 7. When no protective hydroxypropyl cellulose coating is present, the product lost its gastric resistance, particularly when stored at 37° C./80% RH for six weeks. This is presumably due to the effect of humidity on the hydrolysis of the cellulose acetate phthalate polymer, resulting in the formation of phthalic acid and acetic acids. The role of the outer coat may involve inhibition of moisture transfer through the film. There is also some delay in the in vitro release of stored capsules in pH 6.8 buffer solution, among samples stored at 45° C.. The protective coat has no influence on the drug release in pH 6.8 buffered medium.

Figure 7:
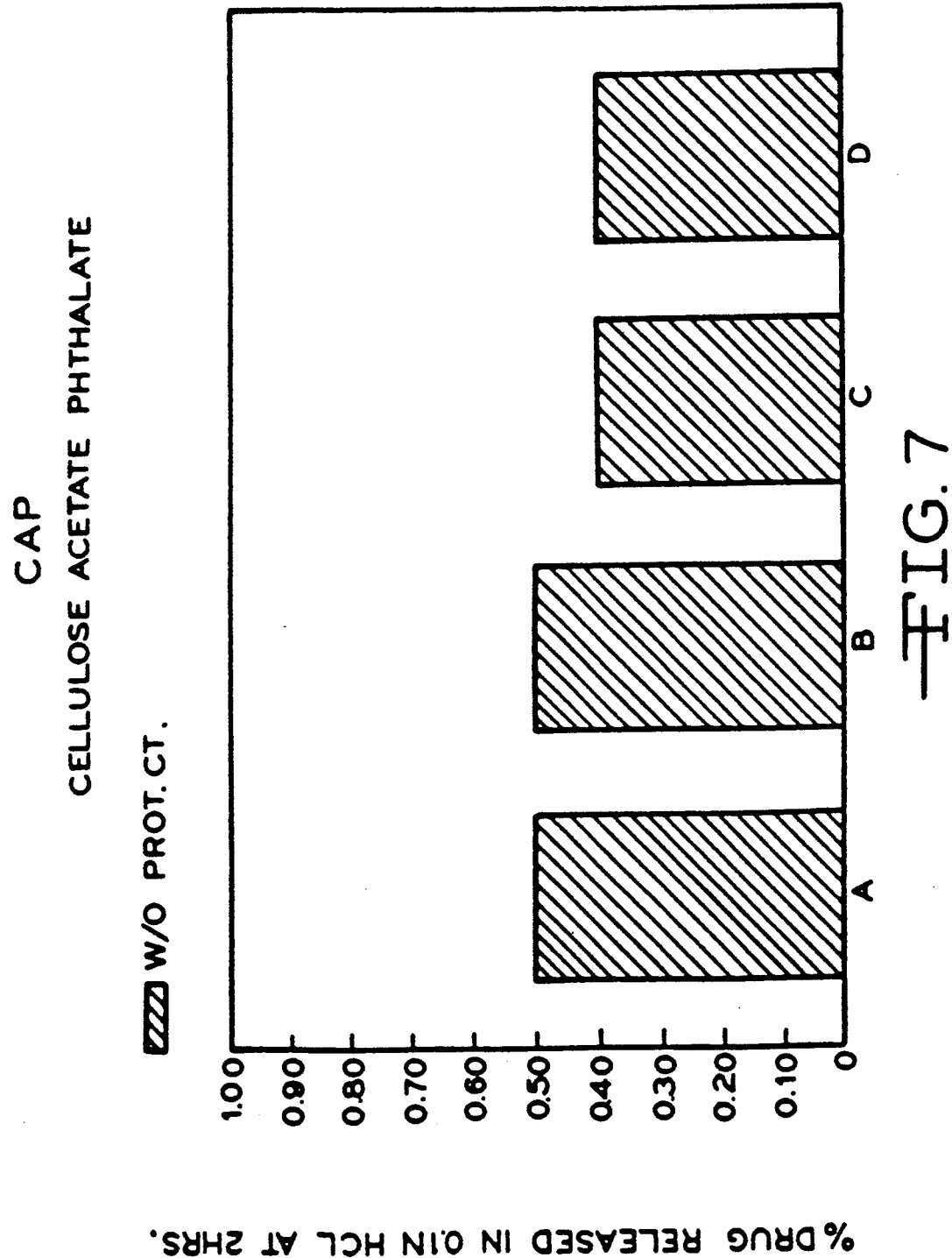
Figure 8:
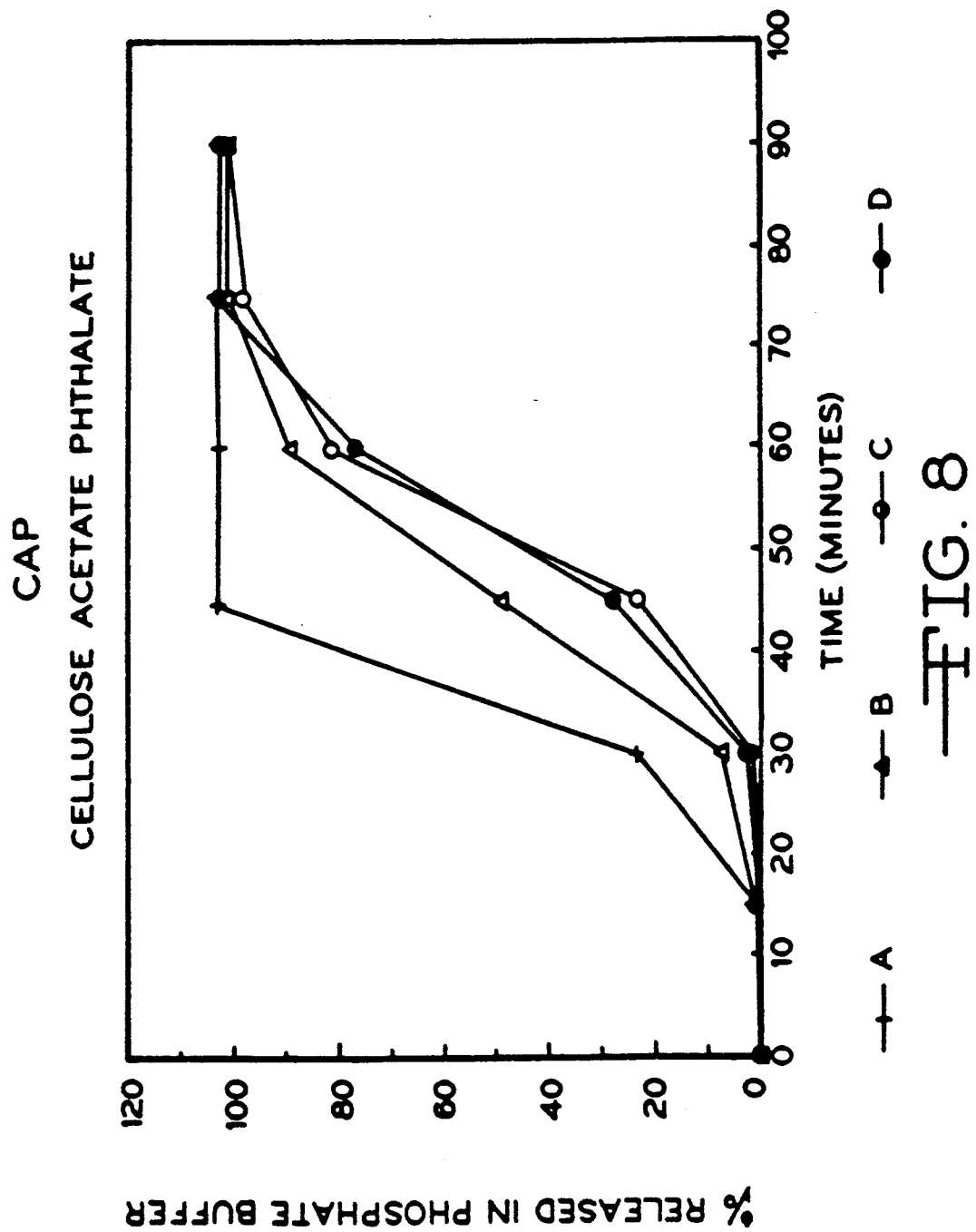

Data similar to the above obtained on cellulose acetate phthalate coated capsules are presented in FIGS. 7 and 8. Even without a protective coat, cellulose acetate phthalate coated capsules are found to be effective in resisting dissolution in gastric fluids as might be expected for polymer applied through an organic medium. However, these capsules exhibit a small delayed release pattern in phosphate buffer pH 6.8 after storage under accelerated conditions.

Figure 9:
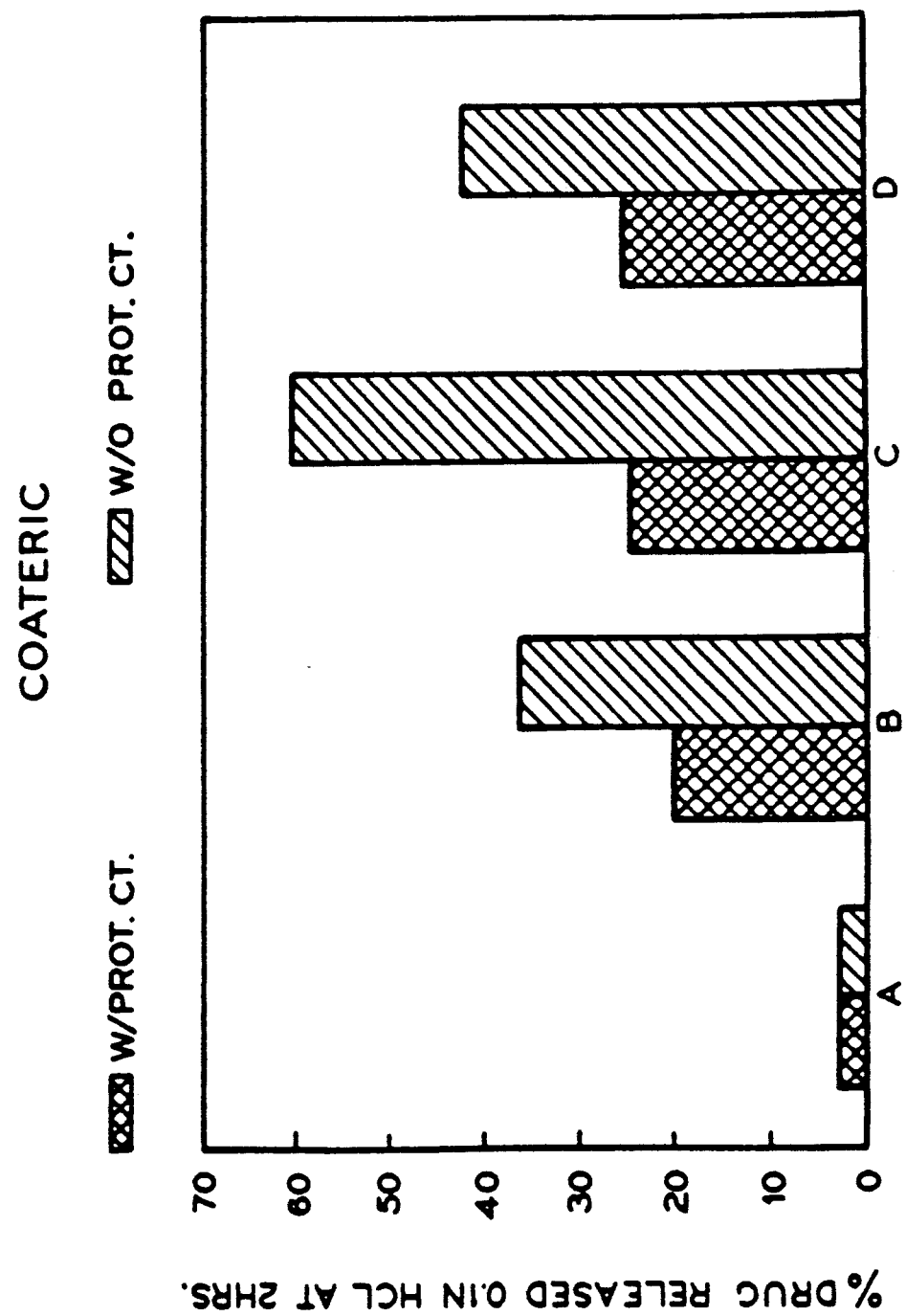
Figure 10:
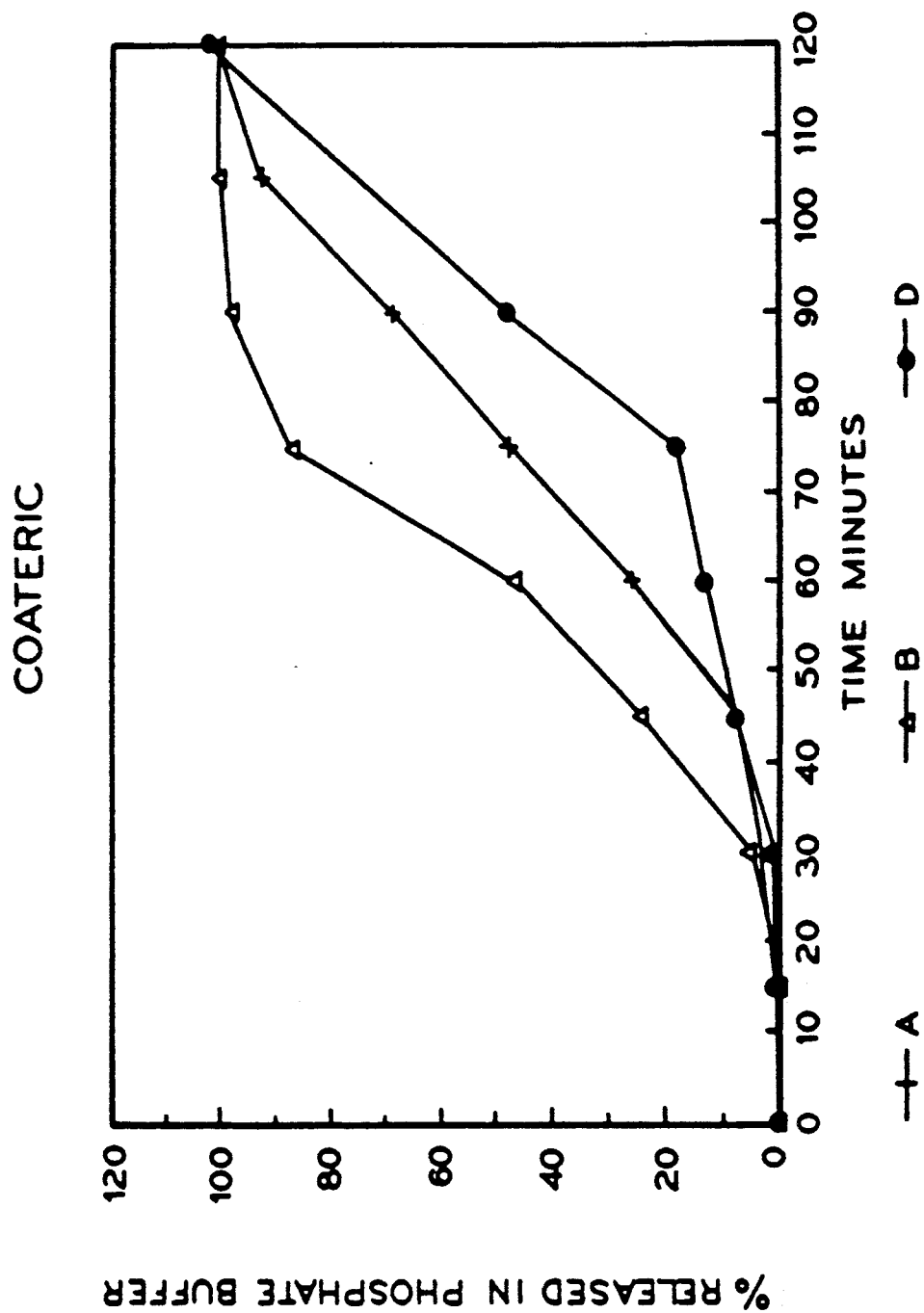

FIGS. 9 and 10 describe the storage data obtained on capsules coated with Coateric ™. Capsules coated with this polymeric system show the greatest instability upon storage. A number of differences become apparent between the capsules coated with Coateric ™ and to those coated with other polymers. First, there is a small amount of drug release in 0.1N HCl after two hours, even when the capsules are coated at a level of 20 mg/cm². Upon storage under stressful conditions, the polymer films cracked, resulting in the loss of gastric resistance with these capsules. Although application of protective coat of hydroxypropyl cellulose aids in promoting the stability of the dosage form, nearly 25% of the drug is in solution at two hours in 0.1N HCl among samples of capsules stored at 37° C./80% RH for six weeks or 45° C. for six weeks. In spite of the fact that these capsules show an extensive change in dissolution properties upon storage, it is not accompanied by significant decomposition of the drug. This is confirmed through chemical assay of capsule contents before and after storage.

Capsules coated with polyvinyl acetate phthalate polymer applied through organic solution adhered to each other in a closed container. Without the application of a final protective coat, the capsules give poor physical stability under all storage conditions including room temperature, within a month. It would appear that for polyvinyl acetate phthalate coatings on capsules, a final seal coat is necessary in order to obtain a viable, stable product.

When a protective over coat is included, polyvinyl acetate phthalate-coated capsules stored at 45° C. gave excellent gastric resistance. However, storage at 37° C./80% RH for six weeks results in 3.5% drug release in acidic fluids in two hours. There is also some slowing of drug dissolution in 0.05M phosphate buffer pH 6.8, although all the label quantity of drug is in solution within 75 minutes. In o comparison with aqueous dispersion of Coateric ™, organic based solutions of polyvinyl acetate phthalate exhibits far greater stability under conditions of high stress storage.

Physicochemical Measurements on Coated Films

The SEM photomicrographs of the various enteric coating films are consistent with the finding of increased dissolution stability. Eudragit ® L30D coats display a smooth homogenous film extending from the gelatin wall through hydroxypropyl cellulose and enteric-coating layer. There is no significant change in the morphology of the coats when examined after storing under various stress conditions. The organic based acrylic films, on the other hand, exhibit a marked change from initial after storage at 37° C./80% room humidity for six weeks. Wrinkling and contraction may predispose to eventual cracking. Microscopic examination of Coateric ™ coated films reveal a porous discontinuous structure even in initial capsule coats. These lines eventually propagate causing cracking which is evident even to the naked eye. It is interesting to note that most of the changes in the film properties are noted when stored at 37° C./80% room humidity, suggesting that a combination of heat and humidity is more detrimental to the integrity of the enteric-coating films than either heat or humidity alone.

Thermal Analysis

DSC: DSC analysis of coated films reveal that all the plasticized films employed in these studies are amorphous; they showed no endothermic or exothermic peaks between 15°-180° C., suggesting that either the glass transition temperatures occur below 15° C. or that specific heat changes that occur in these plasticized systems are too small to be measured accurately. This type of phenomenon is consistent with that noted by other investigators. The inclusion of a plasticizer in the system causes a marked drop in the glass transition temperatures. Additionally, no endothermic peaks, due to the presence of water, are evident in the DSC thermal curves of these plasticized systems.

TMA: TMA analysis of films measures the changes in the physical dimension, e.g. depth of penetration by a loaded probe, of a material under compression, as a function of temperature.

The load applied on the sample is light (3 g), just sufficient to maintain probe contact with the sample throughout the determinations. Care is taken to ensure that no residual moisture is present in the films, as moisture acts as a plasticizer. The thermal curves typically show two softening temperatures, one for hydroxypropyl cellulose layer which occurs at about 60° C. and the other for the enteric polymer. These data indicate that Eudragit ® L30D coated films have a higher softening temperature compared to the other polymeric systems tested. Because of the presence of plasticizer, and more than one layer of coatings on the capsule surface, it is not possible to arrive at definite conclusions regarding the curing or to predict stability of the films based on TMA analysis. Nevertheless, the findings are in general agreement that Eudragit ® L30D films undergo greater penetration at higher temperatures compared to Coateric ™ systems and are less likely to undergo change in stressed systems.

It should be emphasized that these data are obtained in systems containing diethyl phthalate as the plasticizer at a concentration equal to 25% of the polymer. It is probable that each polymeric dispersion or solution functions optimally with a certain plasticizer and surfactant which may be different for a different polymer. Therefore, for Coateric ™ films, use of a plasticizer other than diethyl phthalate, or a combination of plasticizers at different concentrations may have produced better stability profiles. In addition, the application conditions are not optimized here for the various systems. However, one of ordinary skill in the art can readily optimize each system.

Thus, the present invention provides unexpectedly advantageous pharmaceutical dosage forms, and processes of preparation for the fo.ms. A summary of the data of the figures is shown in the following Table 6.

TABLE 6

Effect of Protective Coat on the In Vitro Drug Release of Enteric Coated Capsules in 0.1N Hydrochloric Acid at 50 rpm and 37° C.

| Enteric Polymer | Storage Condition | % Drug in Solution at 2 Hours |
| --- | --- | --- |
| Eudragit ® L30D | Initial | 0.3 |
| (Enteric coat: | 24 h/25° C. | 0.5 |
| 5 mg/cm$^2$) | 37° C./80% RH/6 wks | >20 |
|  | 45° C./6 wks | >20 |
| Eudragit ® L30D | 24 h/25° C. | 0.4 |
| (Enteric coat: | 37° C./80% RH/6 wks | 0.6 |
| 19.2 mg/cm$^2$) | 45° C./6 wks | 0.5 |
| Aquateric ® | Initial | 0.5 |
| (Enteric coat: | 24 h/80% RH | 1.3 |
| 18.8 mg/cm$^2$) | 37° C./80% RH/6 wks | 56.2 |
| w/o protective coat | 45° C./6 wks | 8.0 |
| w/ protective coat | Initial | 0.5 |
| (HPC) | 24 h/80% RH | 0.2 |
|  | 37° C./80% RH/6 wks | 0.8 |
|  | 45° C./6 wks | 0.2 |
| Coateric ™ | Initial | 3.7 |
| (Enteric coat: | 24 h/80% RH | 19.8 |
| 24.0 mg/cm$^2$) | 37° C./80% RH/6 wks | 60.3 |
| w/o protective coat | 45° C./6 wks | 42.5 |

TABLE 6-continued

Effect of Protective Coat on the In Vitro Drug Release of Enteric Coated Capsules in 0.1N Hydrochloric Acid at 50 rpm and 37° C.

| Enteric Polymer | Storage Condition | % Drug in Solution at 2 Hours |
| --- | --- | --- |
| w/ protective coat | Initial | 3.7 |
|  | 24 h/80% RH | — |
|  | 37° C./80% RH/6 wks | 24.5 |
|  | 45° C./6 wks | 25.0 |

We claim:

1. An enteric coated pharmaceutical capsule having acetates or derivatives thereof comprising cellulose acetate phthalate or polyvinyl acetate phthalate as the enteric coatign where in the improvement is an enteric coating level consisting of from 14 mg/cm$_2$ to 24.0 mg/cm$_2$ and a protective coating comprising a hydrophilic coating comprising hydroxypropyl cellulose, hydroxymethyl cellulose or hydroxypropylmethyl cellulose.

2. A dosage form of claim 1 wherein the high enteric coating level comprises enteric coating of 15 mg/cm$^2$.

3. A dosage form of claim 1 wherein the second coating comprises hydroxypropyl cellulose.

4. An enteric coated pharmaceutical capsule having dissolution stability wherein the stability is provided by coating levels consisting of from 14 mg/cm$^2$ to 24.0 mg/cm$^2$ comprising enteric coating wherein the coating is acetates or derivativfes thereof and a second coating comprising hydroxypropyl cellulose, hydroxymethyl celluose or hydroxypropylmethyl cellulose.

5. A dosage form of claim 4 wherein the high enteric coating level comprises enteric coatign of 15 mg/cm$^2$.

6. A dosage form of claim 4 wherein the second coating comprises hydroxypropyl cellulose.

7. An enteric coated pharmaceutical capsule having acrylic resins and derivatives thereof as the enteric coating wherein the improvement is a enteric coating level consisting of from 14 mg/cm$^2$ to 24.0 mg/cm$^2$.

8. A dosage form of claim 4 wherein the high enteric coating level comprises enteric coating of 15 mg/cm$^2$.

* * * * *